United States Patent [19]

Reinson et al.

[11] Patent Number: 5,069,494
[45] Date of Patent: Dec. 3, 1991

[54] DEVICE FOR STORAGE AND INSERTION OF CONTACT LENSES

[75] Inventors: Lorne R. Reinson, White City; Mark J. Akerman, Regina; John Klippenstein, White City, all of Canada

[73] Assignee: Lens-O-Matic Inc., White City, Canada

[21] Appl. No.: 592,456

[22] Filed: Oct. 5, 1990

[51] Int. Cl.⁵ ........................ A61F 9/00; A45C 11/00
[52] U.S. Cl. .................................. 294/1.2; 294/64.1; 206/5.1
[58] Field of Search ............... 294/1.2, 64.1; 206/5.1, 206/535; 220/4.27

[56] References Cited

U.S. PATENT DOCUMENTS

| | | |
|---|---|---|
| 2,919,696 | 1/1960 | Rinaldy . |
| 2,940,589 | 6/1960 | Silverman ...................... 220/4.27 X |
| 3,091,399 | 8/1963 | Leonardos . |
| 3,129,971 | 4/1964 | Kobler . |
| 3,177,874 | 4/1965 | Spriggs . |
| 3,643,672 | 2/1972 | Brown . |
| 3,645,284 | 2/1972 | Krezanoski et al. . |
| 3,791,689 | 2/1974 | Boone et al. . |
| 3,879,076 | 4/1975 | Barnett ............................. 294/1.2 |
| 4,036,357 | 7/1977 | Czelen ................................ 206/5.1 |
| 4,071,272 | 1/1978 | Drdlik . |
| 4,093,291 | 6/1978 | Schurgin ............................ 294/1.2 |
| 4,123,098 | 10/1978 | Shoup . |
| 4,238,134 | 12/1980 | Cointment . |
| 4,429,786 | 2/1984 | Hucal . |
| 5,002,179 | 3/1991 | Dhalla ................................ 206/5.1 |

Primary Examiner—Margaret A. Focarino
Assistant Examiner—Dean J. Kramer
Attorney, Agent, or Firm—Adrian D. Battison; Stanley G. Ade; Murray E. Thrift

[57] ABSTRACT

A device for removing, storing and applying contact lenses comprises a plurality of compartments arranged axially spaced in a cylindrical body with the base of each compartment formed by a portion which can be unscrewed from the remainder and which defines the cover for the next adjacent portion. An end compartment receives an applicaator head which is stored within the compartment in a suitable liquid. The applicator includes a suction bulb and the head which is in the form of a cylindrical body having a peripheral edge of approximately the diameter of the outer edge of the lens and a membrane extending across the cylindrial body. The membrane has an upper surface for engaging the lens which is perforated so that suction applied by the bulb draws the lens onto the membrane and then further suction distorts the membrane to pull the sides of the cylindrical portion inwardly to pinch the lens and break the seal.

11 Claims, 3 Drawing Sheets

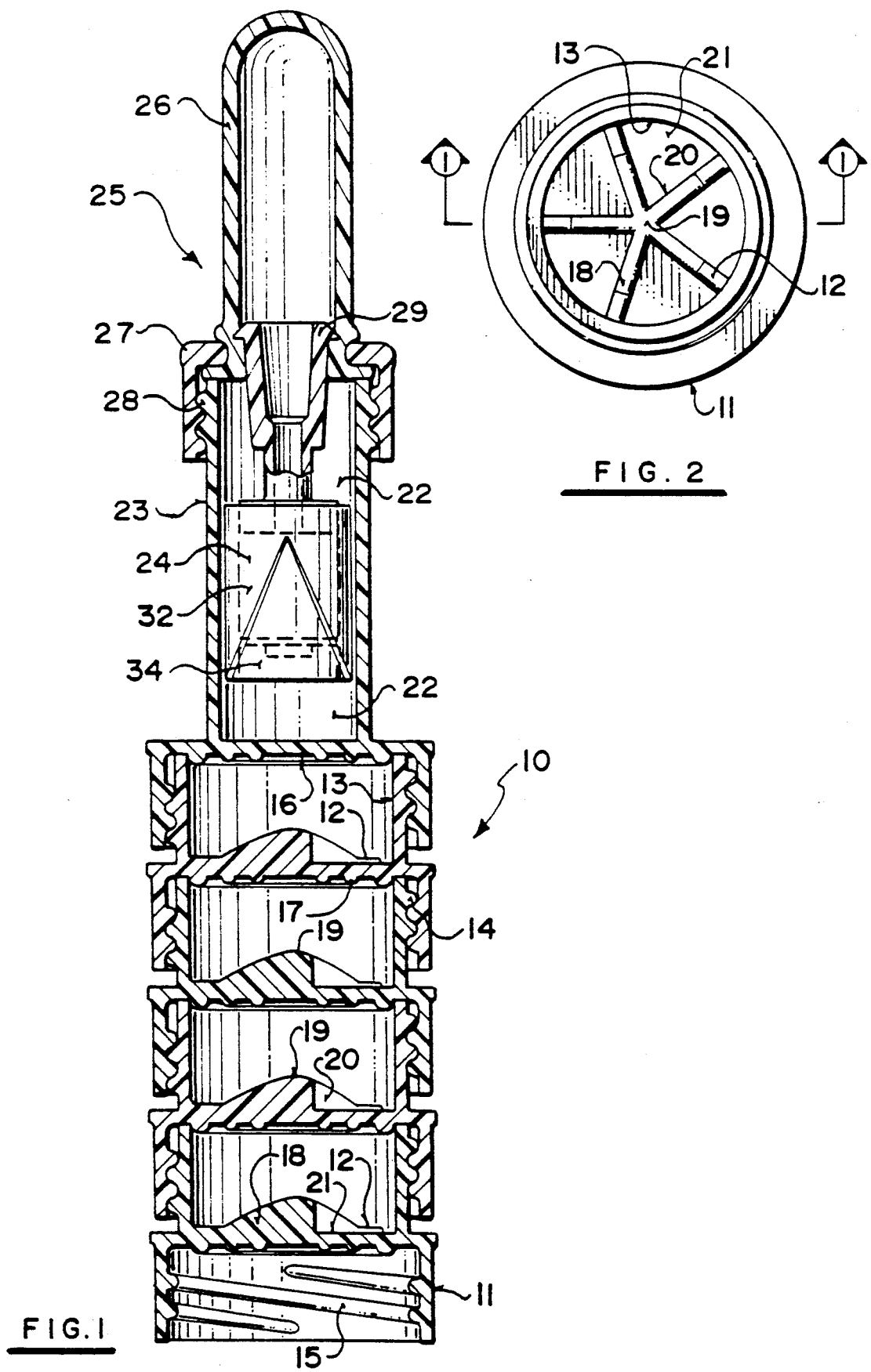

DEVICE FOR STORAGE AND INSERTION OF CONTACT LENSES

BACKGROUND OF THE INVENTION

This invention relates to a device for storage and insertion of contact lenses. As is well known contact lenses have achieved many advances in the past 25 years which have led to widespread use for correction of various sight defects. Soft lenses have particularly increased in popularity in view of their increased comfort and ability to provide extended wear characteristics. Such soft lenses tend to be larger in diameter than hard lenses having an outside diameter approximately equal to or slightly greater than the iris of the eye. This makes them much more difficult to apply to the eye even by experienced users and this difficulty can prevent new users from continuing to use the lenses. In addition the flexibility of the lenses enables them to accommodate closely to the outside shape of the eye and thus the suction forces generated between the eye and the lens can be extremely strong making it difficult to remove the lens. Removal is generally carried out by pinching the lens so that it is squeezed away from the eye thus breaking the seal and enabling the lens to be pulled away from the eye.

This is normally carried out by the fingers of the wearer which necessarily causes the lens to be handled and thus come into contact with any foreign bodies or contamination on the fingers of the wearer.

Various proposals have been made dating back to 1958 for devices to assist in storing and applying contact lenses.

Various arrangements have been proposed for suction cups of various different types for example as shown in U.S. Pat. No. 3,791,689 (Boone—issued Feb. 12, 1974), U.S. Pat. No. 4,071,272 (Drdlik—issued Jan. 31, 1978) and U.S. Pat. No. 4,123,098 (Shoup—issued Oct. 31, 1978). All of these devices generally comprise a simple suction head which has a diameter of the order of the diameter of the lens with a bulb device at one end of a tube connected to the cup which can be compressed and released to generate a suction by which the lens can be picked up and applied to the eye.

However in practice this has been found not to be correct since the suction forces which adhere the lens to the eye can be sufficiently strong that the eyeball is pulled from its socket before the lens to eye seal is broken.

U.S. Pat. No. 4,238,134 (Cointment—issued Dec. 9, 1980) notes the difficulty of breaking the fluid suction-bond of the lens to the eye and proposes an arrangement in which a soft rimmed cup is placed on the lens and the cup then manually squeezed inwardly so the edges of the cup grasp the lens and tend to pinch it off the eye in the same way as the fingers of the user are normally used.

This arrangement is however not satisfactory in that it merely provides additional surfaces separate from the finger of the user which act in the same way as the fingers of the user and thus tend to pinch the lens together. It is difficult therefore for the user to handle the lens once it has been pinched off the eye since the user must then release the cup in order to deposit the lens into a soaking solution.

For these reasons, therefore, none of the above devices is currently available for sale and none has been successful in assisting users of contact lenses in the hygienic and effective, storage and application of the lenses to the eye.

It is one object of the present invention, therefore, to provide an improved device for storage and insertion of contact lenses.

According to a first aspect of the invention, therefore, there is provided a device for application to the eye of a wearer of a soft contact lens, the device comprising means for generating a suction and a head member mounted on said suction means for transmission of suction thereto and arranged for engaging and grasping the contact lens, said head member including suction communication means arranged to transmit said suction to said lens to hold said lens on said head member, peripheral grasping means the lens at or adjacent its periphery comprising a peripheral edge of a generally cylindrical body having an axis extending away from said lens generally at right angles thereto said suction communication means including a suction cup member inwardly of said peripheral edge.

It is a further object of the present invention to provide an improved device of this type which enables the head member and lenses to be properly and hygienically stored when not in use.

According to a second aspect of the invention therefore, there is provided a device for removal from, storage and application to the eye of a wearer of a pair of soft contact lenses, the device comprising means for generating a suction, a head member mounted on said suction means for transmission of suction thereto and arranged for engaging and grasping one of the pair of contact lenses, and a container having a first compartment shaped to receive said head member and arranged so as to engage said suction means for closing said first compartment to contain a storage liquid therein and a second and third compartment each including means for closing the respective compartments for receiving and storing a respective one of the lenses therein in a storage liquid.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

FIG. 1 is a cross-sectional view through a cylindrical container for receiving the lenses and for receiving a suction bulb and head member for applying and removing the lenses according to the invention.

FIG. 2 is a cross-sectional view along the lines 2—2 of FIG. 1.

In the drawings like characters of reference indicate corresponding parts in the different figures.

DETAILED DESCRIPTION

Figure 3:
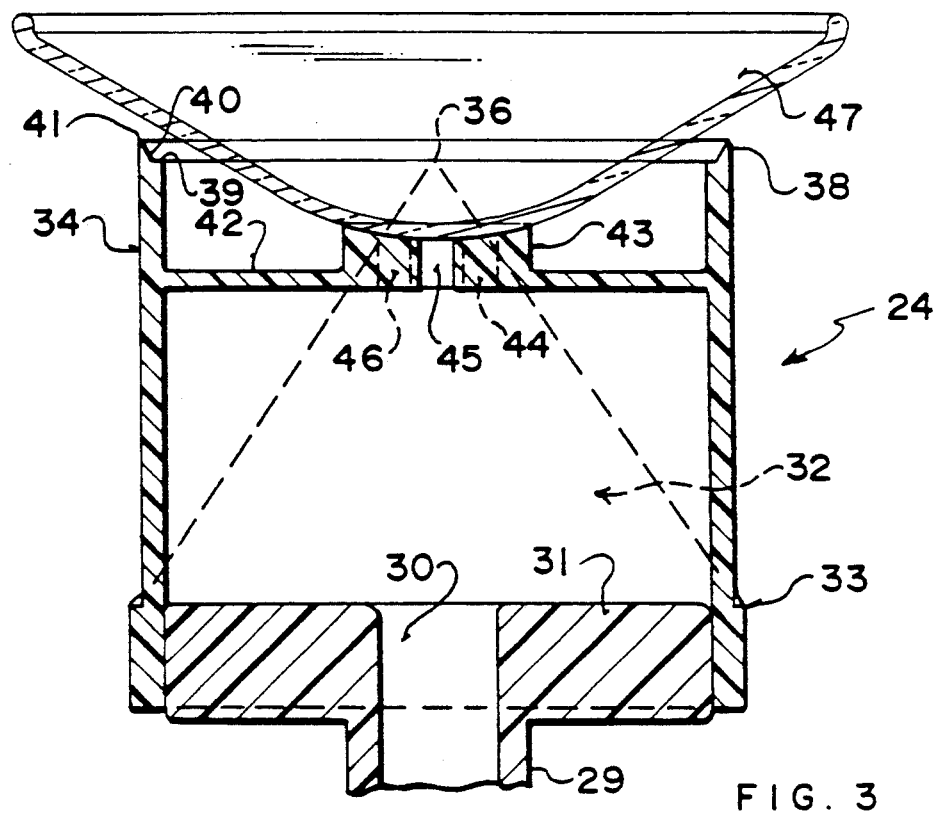
FIG. 3 is an enlarged cross-sectional view of the head member of FIG. 1.

The container for the lenses and for the head of the applicator is generally indicated at 10 and is formed from a plurality of separate pieces. Each of the pieces is generally cylindrical in shape so that the pieces can be screwed together in co-axial arrangement so as to form a generally cylindrical body constituting the container 10.

Thus the container comprises a plurality of lens receiving portions 11 of which there are four such portions shown in FIG. 1 each for receiving a lens so that four such lenses can be stored thus providing a first pair and a back-up pair. In some cases the user may require to store only two such lenses in which case two of the portions 11 will be simply removed by unscrewing.

Each of the portions 11 comprises a base 12 upon which the contact lens can rest, a surrounding retaining wall or rim 13 for containing a fluid around the lens and an external screw thread 14 on an outer surface of the cylindrical retaining wall 13. The external screw thread 14 cooperates with an internal screw thread 15 on an underside of the next adjacent portion 11. A cover surface 16 of the next adjacent portion 11 defines a closure for the cylindrical receiving area defined by the base 12, the wall 13 and the under surface 16.

The under surface 16 is generally flat with a plurality of rings outstanding from the surface thereof so as to project downwardly to the base 12 when the portions are attached together. The rings indicated at 17 assist in preventing the lens from moving from its properly positioned location on the base 12 and from adhering to the under surface 16 defining the cover.

Upon the base 12 is a projection 18 arranged centrally of the base 12 and extending upwardly therefrom. An upper surface of the projection 18 is convex in shape of a curvature approximating that of a lens so that the concave surface of the lens can sit directly upon the projection with the convex surface of the lens projecting upwardly therefrom. The projection is formed from five legs which extend outwardly from the central uppermost portion 19 of the projection, each of the legs being indicated at 20. In between each leg and the next equidistantly angularly spaced leg is a space 21 exposing the base 12. This construction of the projection formed by the legs and having the curvature of the lens acts to locate the lens so that it is prevented from slipping off the projection even when the container is shaken or inverted and yet avoids any suction forces being generated between the lens and the projection. The lens therefore when placed in the container in the inverted condition, that is with the convex shape upwardly, remains in that condition despite any handling of the container when the container is closed by application of the cover formed by the next adjacent portion 11.

Separate from the containers for the lenses is provided a compartment 22 defined by a wall 23 which is co-axial with the outer surfaces of the portions 11 but is reduced in diameter relative thereto. The compartment 22 is of increased axial length relative to the compartments for the lenses for receiving a head member 24 of the applicator indicated generally at 25.

The applicator 25 comprises a flexible bulb 26 which is attached to a rigid plastics portion 27 defining a screw thread 28 by which the applicator can be attached to the compartment 22 to close the compartment for receiving a storage liquid.

An extension portion 29 which is flexible extends from the screw threaded plastics portion 27 into the compartment 22 and defines a duct 30 therein. The duct 30 communicates with the interior of the bulb 26 so that compression and release of the bulb generates suction within the duct 30 through the flexible portion 29 for communication to the head 24. When the head 24 is positioned within the compartment 22, application of compression and release to the bulb 26 acts to draw liquid into the head so that it stores liquid inside the head and inside the duct 30 so that any suction forces are communicated hydrostatically that is through the liquid rather than through the medium of air.

The head 24 is formed as a separate disposable item which can be simply applied to and removed from a cylindrical receptor 31 at the end of the flexible member 29. Thus the head 24 can be thrown away after each use if required by the wearer for particularly rigorous hygiene or if required by opticians using the head for different patients.

The head comprises a cylindrical sleeve 32 which is formed of a flexible plastics or rubber material. The sleeve 32 has at one end 33 a portion of greater wall thickness which may be of the order of 1 millimeter for engaging over the receptor 31.

Figure 6:
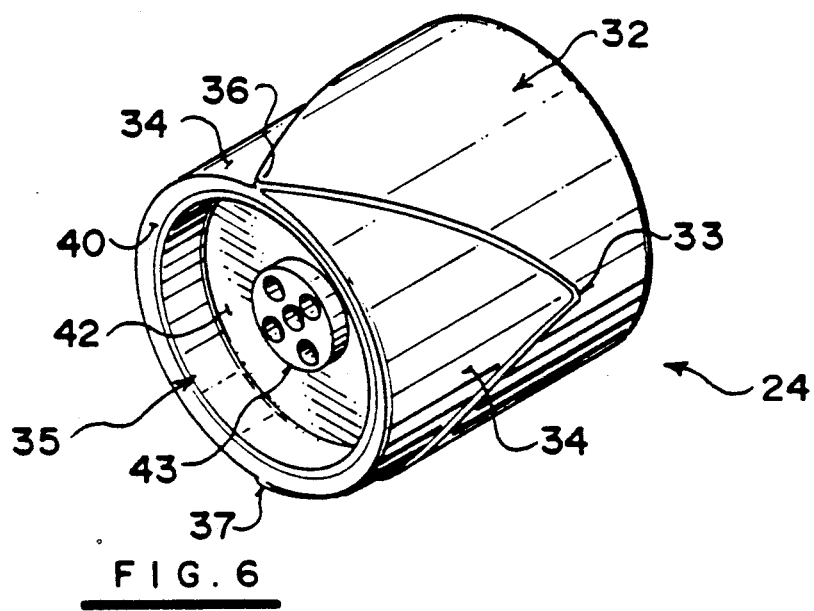
FIG. 6 is an isometric view of the head member of FIGS. 3, 4 and 5.

As shown best in FIG. 6, the cylinder 32 includes two thinner wall portions 34 and 35 which commence at the base of a V-shape adjacent the end 33 and then widen out so as to converge to a pair of ribs 36, 37 at a peripheral edge 38 remote from the end 33. The thickness of the thinner wall portions 34 and 35 is of the order of ½ millimeter so that the cylinder is less resistant to deformation in these areas.

The peripheral edge 38 as best shown in FIG. 3 is shaped so as to define an annular surface 39 as a tapering surface 40 both of which act to reduce the thickness of the wall down to a substantially sharp edge 41 fully surrounding the periphery of the cylinder.

A membrane 42 is secured around the inner surface of the sleeve 32 so that the membrane effectively closes the hollow interior of the sleeve 32. The membrane is of a thin flexible nature having a thickness of the order of ½ millimeter so that it can readily distort on application thereto of relatively low suction forces. A central upstanding portion 43 of the membrane is of increased thickness and defines therethrough a plurality of holes 44 which in the example shown comprise a central hole 45 and four surrounding holes 46. It will be noted that the holes are arranged around the periphery of the central raised area 43 so that they are not on the line joining the ribs 36 and 37 but are offset from that line.

Figure 4:
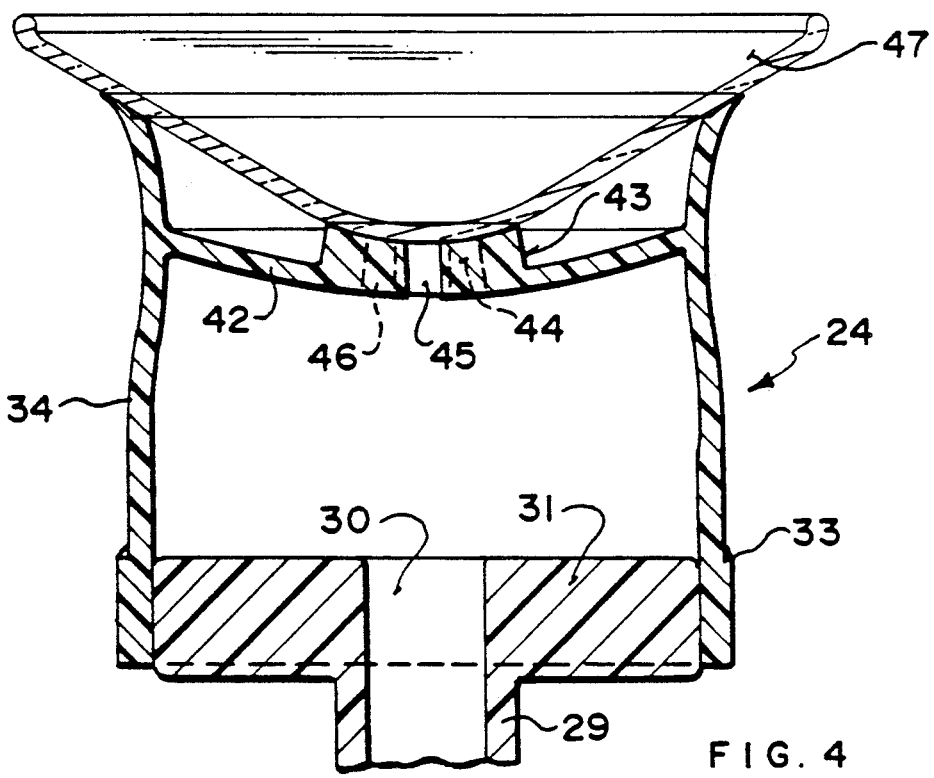
FIG. 4 is a similar view of the head member of FIG. 3 showing it in an operating condition for removing the lens from the eye.
Figure 5:
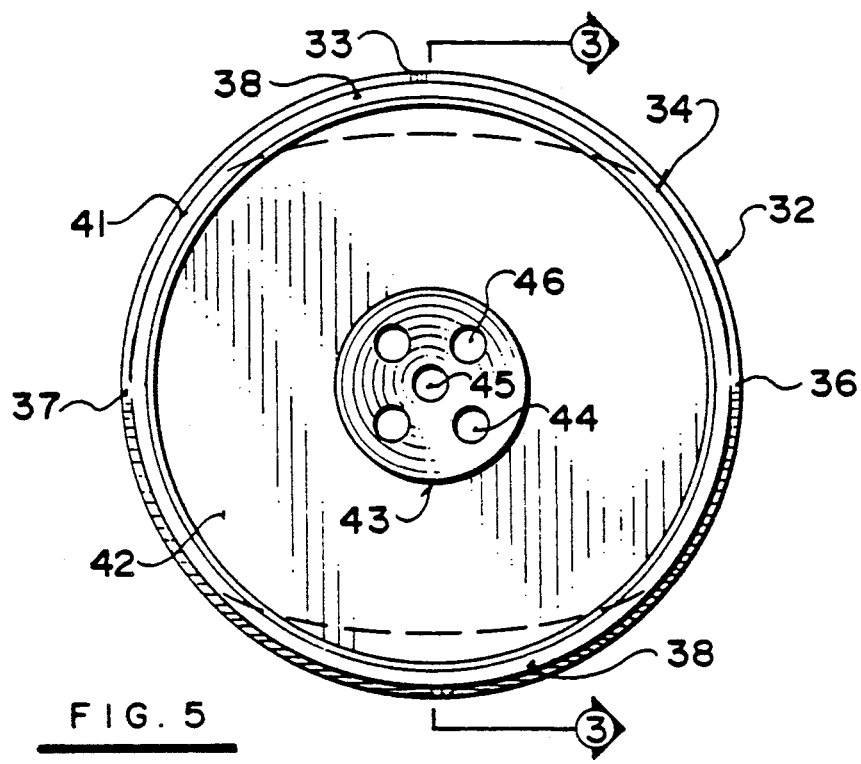
FIG. 5 is a front elevational view of the head member of FIGS. 3 and 4.

The upper surface of the raised portion 43 is part spherical having a radius of curvature substantially equal to that of the convex surface of the lens. The edge 41 has a diameter approximately equal to or slightly less than the outer diameter of a lens one of which is indicated in FIGS. 3 and 4 at 47. The axial position of the edge 41 is such that it is slightly spaced from the lens 47 when the curved upper surface of the raised portion 43 first contacts the center portion of the lens with the membrane flat in the position shown in FIG. 3.

In operation, the uppermost compartment defined by the wall 23 is unscrewed from the first lens storing portion 11 so as to expose the compartment within which the first lens is stored upon the base 12. The lens thus is exposed upwardly with its convex surface uppermost.

The head 24 is at this stage stored within the storage liquid in the compartment 22. The portion 27 is then unscrewed from the compartment 22 so the head 24 can be removed from the liquid. Prior to removal, the bulb 26 can be depressed and released to draw some of the liquid into the head upstream of the membrane 42. Thus the membrane is effectively surrounded by liquid and is fully wetted by same.

The bulb is then slightly depressed and the head brought up to the lens in the portion 11. A slight depression of the bulb when released merely generates enough suction so that the lens is held in place against the surface of the raised portion 43. The suction is communicated through the liquid to the back of the lens at a plurality of location thereon. The lens can then be withdrawn from the portion 11, carried by the head 24 and brought up to the eye of the wearer and attached to the eye of the wearer so that the suction of the lens/eye bond holds the lens against the eye so that it can be released from the raised portion 43 by a simple compression of the bulb 26 which causes the liquid drawn unto the head to be expelled to push the lens onto the eye.

In the reverse process, when it is required to remove the lens from the eye for storage within the portion 11, the head 24 is again removed from its position in the storage compartment 22 within the storage liquid with some liquid drawn into the area of the head 24. The bulb 26 is then more vigorously compressed and the head brought toward the lens on the eye of the wearer. Initially again the central raised portion 43 engages the lens as best shown in FIG. 3. As the bulb 26 is then released, suction is generated in the duct 30 and thus rearwardly of the membrane 42. As the holes 44 are closed by the lens 47 and particularly by the lubrication provided by the liquid between the lens and the raised central portion 43, any further suction generated by the bulb 26 acts to pull against the membrane 42 tending to withdraw it axially along the sleeve 32. As the ends of the membrane are firmly attached to or integral with the inner surface of the sleeve 32, this tends to draw in he sides of the sleeve 32 preferentially at the thinner portions of the wall as indicated at 34 and 35. This condition is shown best in FIG. 4. Thus as the membrane is drawn downwardly or away from the eye generally at right angles thereto, the edge 41 initially contacts the lens at or adjacent its periphery and then tends to move inwardly, preferentially at the thinner portions, so as to pinch the lens and draw the edges of the lens into a ridge away from the eye. This action breaks the lens to eye bond by gradually introducing air from the pinched portion toward the center of the lens so that it can be pulled away from the eye with very little suction force applied directly to the eye.

Thus the suction generated by the bulb 26 firstly holds the lens to the membrane 42 and thus to the head 24 and secondly automatically pinches the lens to break the lens to eye bond while the lens is maintained grasped by the suction at the membrane. There is no necessity for the fingers of the user to in any way approach the lens or the head 24 and the only manual actuation is applied at the bulb 26 the exterior of which does not in any way need to be hygienic.

The lens carried by the membrane 42 can then be returned to the portion 11 and introduced into the portion. 11 directly onto the projection 18 and dropped onto that projection by compressing the bulb 26. Further fluid can then be added to the compartment around the lens and the compartment closed by application of the cover thereto on the base of the next adjacent portion 11 or on the base of the compartment 22. The head 24 can then be returned to the compartment 22 for hygienic storage or can be replaced by a further head if required.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. A device for storage of and for application to the eye of a wearer of a pair of contact lenses, the device comprising suction means for generating a suction and a head member mounted on said suction means for transmission of suction thereto and arranged for engaging and grasping the contact lens, said head member including suction communication means arranged to transmit said suction to said lens to hold said lens on said member, container means defining a first container for receiving liquid, said first container having a base for resting on a support surface and an open top, said suction means including cap means for engaging onto and closing said open top of said first container whereby the head member is stored in the liquid, said head member being arranged such that said suction means is arranged to draw said liquid into said head member whereby said suction is communicated to said lens by contact of said liquid with said lens, said container means including a second and a third container each separate from the first container and each including means for sealingly closing the respective container such that the container is arranged for receiving and storing a lens stored separately from said first container.

2. The invention according to claim 1 wherein said head member is readily separable from said suction means for ready replacement of said head member.

3. The device according to claim 1 wherein said second and third containers comprise a series of co-axially arranged containers each having a base forming a cover for a next adjacent one of the containers whereby the base of each can be screw threaded onto the cover of the next adjacent to define an area therebetween fo receiving said liquid and said lens.

4. The device according to claim 1 wherein each of said second and third containers includes a base for resting on a support surface and an open top, an upper surface of the base having an upstanding projection member having an upper surface defining a curvature substantially equal to that of a concave surface of said lens whereby said lens is stored with a convex surface thereof uppermost for engagement by said head member.

5. The device according to claim 4 wherein said projection member is formed from a plurality of legs extending radially outwardly from a central uppermost portion, each leg being separated from the next.

6. The device according to claim 4 wherein the first container comprises a base forming a cover for one of said second and third containers, an elongate tube extending from said base coaxially with said second and third containers, said open top being defined at an end of said tube remote from the base and means at said open top for cooperating with said cap means of said suction means for sealingly closing said first container.

7. The device according to claim 6 wherein the tube is cylindrical and wherein the base has a circular outer periphery, the tube having a smaller diameter than the outer periphery of the base.

8. The device according to claim 1 wherein the head member includes an end surface shaped for acting upon a convex surface of the lens, the end surface including means for communicating said liquid from the head member to the convex surface of the lens at a plurality of locations thereon.

9. The device according to claim 8 wherein the end surface has projecting means thereon for engaging the convex surface of the lens and surface portions thereon recessed from the projecting means for receiving liquid between the surface portions and the convex surface of the lens.

10. The device according to claim 1 wherein the suction means includes said cap means, a suction bulb extending from said cap means away from said first container, said suction communicating means including a tubular portion thereof extending through a central opening of the cap into the suction bulb, the head member being flexible and comprising a tube coaxially surrounding a projecting tube of the communicating means.

11. A method for storage of and for application to the eye of a wearer of a pair of contact lenses, the method comprising providing a first container having a base for resting on a support surface and an open top, providing a suction member including a cap for the open top, a suction bulb, a suction duct and an end face communicating with the suction duct and arranged for engaging the contact lens, storing the end face in the container immersed in a storage liquid, providing a second and a third container separate from the first container each for receiving a respective one of the pair of contact lenses and including means therein for supporting the contact lens with a convex surface of the contact lens presented upwardly for engagement with the end face, storing each of the pair of the contact lenses in a respective one of the second and third containers immersed in liquid, squeezing the bulb while the end face remains in the first container to draw a portion of said liquid into the suction duct, moving the end face into contact with the convex surface of one of the lenses, releasing the bulb to apply suction through the end face to the convex surface, communicating the suction from the suction duct through the end face to the convex surface through liquid carried between the convex surface and the end face, lifting the lens from the respective one of the second and third containers, transferring the lens to the eye of the wearer and forcing liquid from the suction duct to the end face to release the lens into the eye.

* * * * *